(12) United States Patent
Duhamel et al.

(10) Patent No.: US 8,119,399 B2
(45) Date of Patent: Feb. 21, 2012

(54) METHOD AND SYSTEM FOR COLLECTING CELLS OF A BIOLOGICAL SPECIMEN

(75) Inventors: Eric V. Duhamel, Nashua, NH (US); Tuan Ha, Randolph, MA (US)

(73) Assignee: Cytyc Corporation, Marlborough, MA (US)

( * ) Notice: Subject to any disclaimer, the term of this patent is extended or adjusted under 35 U.S.C. 154(b) by 1334 days.

(21) Appl. No.: 11/610,395

(22) Filed: Dec. 13, 2006

(65) Prior Publication Data
US 2008/0142456 A1     Jun. 19, 2008

(51) Int. Cl.
*C12N 5/00*     (2006.01)
(52) U.S. Cl. ......... 435/325; 210/348; 210/406; 210/808
(58) Field of Classification Search ....................... None
See application file for complete search history.

(56) References Cited

U.S. PATENT DOCUMENTS

| 6,010,909 A | * | 1/2000 | Lapidus | .......... 436/63 |
| 2003/0100125 A1 | | 5/2003 | Pressman | |
| 2004/0065622 A1 | | 4/2004 | Ferguson | |
| 2004/0069714 A1 | | 4/2004 | Ferguson | |

OTHER PUBLICATIONS

PCT International Search Report for PCT/US2007/086296, mailed Jun. 2, 2008, forms PCT/ISA/220 and 210, Applicant Cytyc Corporation, (6 pages).
PCT Written Opinion of the International Searching Authority for PCT/US2007/086296, mailed Jun. 2, 2008, form PCT/ISA/237, Applicant Cytyc Corporation, (7 pages).

* cited by examiner

*Primary Examiner* — Kade Ariani
(74) *Attorney, Agent, or Firm* — Vista IP Law Group LLP (57) ABSTRACT

A method for determining when sufficient cells of a biological specimen have been collected by a filter is based on measuring an air flow rate between a filter and a vacuum source. The air flow rate can be measured by a mass air flow sensor. The air flow rate dropping below a threshold, such as a certain percentage of an initial or baseline flow rate, indicates that sufficient cells have been collected to provide sufficient filter coverage.

16 Claims, 7 Drawing Sheets

Filter Face — About 20% Coverage

FIG. 11

METHOD AND SYSTEM FOR COLLECTING CELLS OF A BIOLOGICAL SPECIMEN

FIELD OF INVENTION

The present invention relates to preparing samples of biological specimens and, more particularly, to determining when a cell collection filter of a slide preparation system has been sufficiently covered with cells of a biological specimen.

BACKGROUND

Medical professionals and technicians often prepare biological specimens on a specimen carrier, such as a slide, and review the specimens to analyze whether a patient has or may have a particular medical condition or disease. For example, a biological specimen, such as a cytological specimen, is examined to detect malignant or pre-malignant cells as part of a Papanicolaou (Pap) smear test and other cancer detection tests. After a specimen slide has been prepared, automated systems are used to focus the technician's attention on the most pertinent cells or groups of cells, while discarding less relevant cells from further review.

Figure 1:
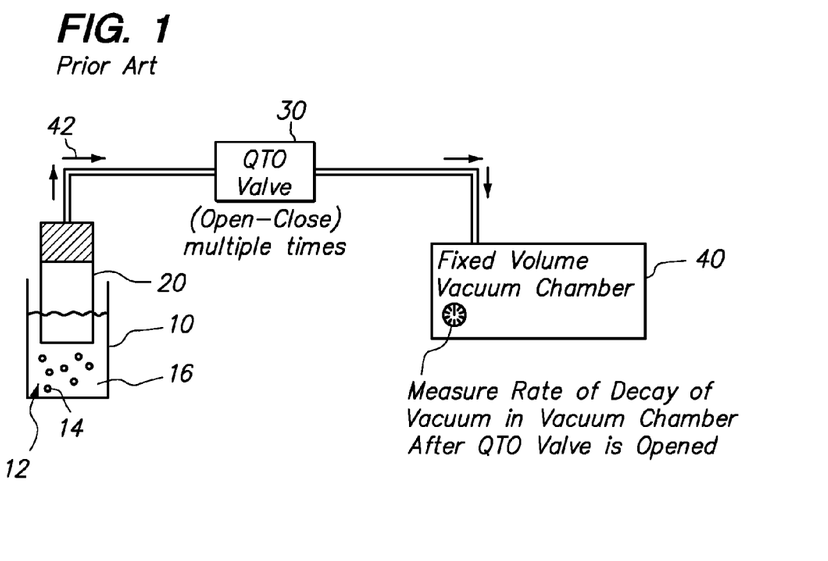
FIG. 1 illustrates a known system for determining how much of a filter is covered by cells of a specimen based on measuring vacuum levels and determining the rate of decay of vacuum in a fixed volume vacuum chamber.

Referring to FIG. 1, one known automated slide preparation system includes a container or vial 10 that holds a biological specimen 12, a filter 20, a valve 30 and a fixed volume vacuum chamber 40. The specimen 12 typically includes multiple cells 14 that are dispersed within a liquid, solution or transport medium 16, such as PreserveCyt, available from Cytyc Corporation (www.cytyc.com). One end of the filter 20 is disposed in the liquid 16, and the other end of the filter 16 is coupled through the valve 30 to the fixed volume vacuum chamber 40. When the valve 30 is opened, vacuum or negative pressure 42 from the fixed volume vacuum chamber 40 is applied to the filter 20 which, in turn, draws or sips liquid 16 up into the filter 20. Cells in the drawn liquid are collected by face or bottom of the filter 20.

It is desirable to collect a sufficient number of cells on the filter to provide a sampling of cells with desired distribution and (limited) thickness. Collecting too many cells can complicate subsequent viewing of the collected by a cytotechnologist or by an inspection or imaging system. For example, cells may crowd other cells and can be stacked on top of each other. This may cause selected cells to be hidden or overlooked when they should have been reviewed. On the other hand, inadequate filter coverage may result in incomplete or inaccurate results, which may also result in cells that should have been reviewed not being collected and reviewed at all.

With the known system shown in FIG. 1, however, collecting the desired number of cells is not as easy as simply turning the valve 30 and applying a vacuum 42 from the fixed volume vacuum source. Rather, multiple iterations of opening and closing the valve and re-evacuating the fixed volume vacuum chamber must be performed.

Figure 2:
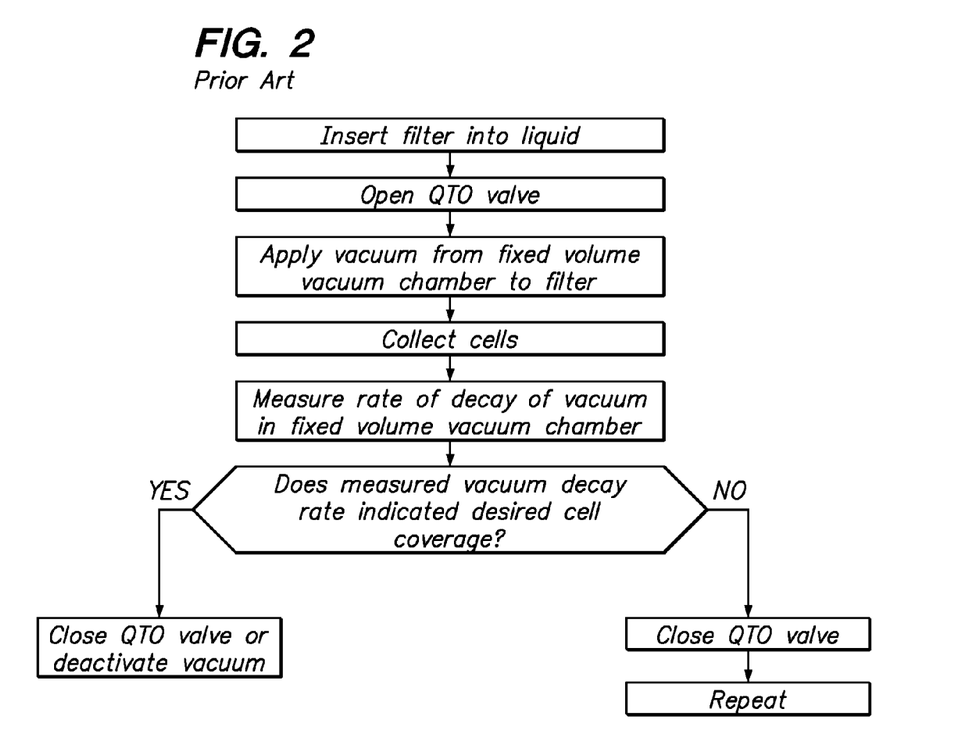
FIG. 2 is a flow chart illustrating a known method that is performed using the system shown in FIG. 1.

More particularly, referring to FIG. 2, the cell collection process typically begins by evacuating the fixed volume vacuum chamber 40, if it is not already evacuated, to a suitable negative pressure level. The valve 30 is then opened to apply a vacuum 42 from the chamber 40 to the filter 20 to collect cells 14 against the filter 20. Since the vacuum chamber 40 is a fixed volume vacuum chamber, the vacuum level decreases as cells 14 are collected. The rate of decay of the vacuum level in the vacuum chamber is monitored using a vacuum level indicator 44 or other suitable device over time. The rate of decay of the vacuum level in the chamber 40 is used to indicate the amount of cell coverage on the filter 20.

The vacuum level decays faster when the filter has no cells or only a few cells compared to when the filter has collected a larger number of cells.

A determination is made whether or not the filter has sufficient cell coverage based on whether the rate of vacuum decay drops to a certain value from the maximum initial value. During the initial application of vacuum 42, cells 14 are collected by the filter 20. However, the quantity of cells collected usually is not sufficient. Consequently, vacuum 42 must be applied again to the filter 20 to collect additional cells 14.

However, since the vacuum chamber 40 is a fixed volume vacuum chamber and was already evacuated, the vacuum chamber 40 must be re-evacuated. Thus, after each time cells 14 are collected, the valve 30 is closed, the fixed volume vacuum chamber 40 is re-evacuated in order to provide a vacuum environment, and the valve 30 is opened to apply vacuum 42 to the filter 20 to collect additional cells 14. These steps are repeated until the rate at which the vacuum level decays in the fixed volume vacuum chamber drops to a certain level to indicate that sufficient cells 14 have been collected to provide sufficient filter 20 coverage. It may be necessary to repeat these steps many times, e.g., as many as 12-24 times, in order to obtain the desired amount of filter coverage. These steps can require substantial processing time, e.g., 30 seconds, which can quickly multiply to result in processing inefficiencies as more slides are prepared.

In addition to longer processing and preparation times, known systems also typically use a more complicated valve 30. Since the valve 30 is opened and closed so many times, it is desirable and/or necessary that the valve 30 be able to open and close quickly to reduce processing times. Thus, the valve 30 that is used in known systems is often referred to as a "Quick Turn Open" valve or "QTO" valve, as shown in FIG. 1. QTO valves are typically more expensive than other valves, thereby increasing the cost of slide preparation systems.

While known systems and methods have allowed cytotechnologists to effectively prepare slides for subsequent analysis, they can be improved. It would be advantageous to provide a more cost and time efficient slide processing system. It would also be desirable to eliminate repetitive iterations of opening a valve, measuring the decay rate of vacuum within the fixed volume vacuum chamber, closing the valve, and re-evacuating the vacuum chamber until sufficient cells have been collected. Doing so would significantly decrease processing and slide preparation times. Further, it would be advantageous to eliminate the QTO valve, since this valve can be relatively expensive to provide and maintain.

SUMMARY

One embodiment is directed to a method for collecting cells from a biological specimen, such as a cytological specimen. The method includes applying a vacuum to the filter to collect cells of the specimen and measuring a rate of air flow between the filter and a vacuum source. The method also includes determining when sufficient cells have been collected by the filter based on the measured air flow rate.

Another embodiment is directed to a method for collecting cells from a biological specimen, such as a cytological specimen, and includes determining a baseline air flow rate, applying a vacuum from a vacuum source to a filter to collect cells of the specimen and measuring an air flow rate between the filter and the vacuum source. The method further includes determining when sufficient cells have been collected by the filter based on the measured air flow rate dropping below the baseline air flow rate by a predetermined amount.

In an alternative embodiment, a system for collecting cells from a biological specimen, such as a cytological specimen, held in a container includes a vacuum source, an air flow sensor and a controller. The vacuum source provides negative pressure to a filter at least partially disposed in the specimen so that cells of the biological specimen are collected by the filter. The air flow sensor is positioned between the filter and the vacuum source and measures an air flow rate while cells are collected by the filter. The controller receives the measured air flow rate from the air flow sensor and determines when sufficient cells have been collected by the filter based on the measured air flow rate.

In various embodiments, the vacuum that is applied to the filter can be a constant vacuum. With a constant vacuum, as cells are collected by the filter, the measured air flow rate decreases in an approximately linear manner relative to filter coverage.

In various embodiments, a mass air flow sensor can be used to measure the air flow rate. The mass air flow sensor can be positioned between the filter and a valve that controls application of the vacuum to the specimen. Alternatively, the mass air flow sensor can be positioned between a vacuum source and a valve that controls application of the vacuum to the specimen Additionally, in various embodiments, a determination is made that sufficient cells have been collected by the filter based on the measured air flow rate dropping below a threshold air flow rate, which can be determined relative to the baseline air flow rate. For example, the threshold air flow rate can be about 80% of the baseline air flow rate. A determination can be made that about 20% of a face of a filter is covered with cells when the measured air flow rate is about 80% of the baseline air flow rate.

Other aspects of embodiments are described herein and will become apparent upon reading the following detailed description with reference to the accompanying drawings.

BRIEF DESCRIPTION OF THE DRAWINGS

Embodiments of the invention will be described and explained with additional specificity and detail through the use of the accompanying drawings in which.

DETAILED DESCRIPTION OF ILLUSTRATED EMBODIMENTS

Embodiments of a system and method for determining when sufficient filter coverage has been achieved based on measurements of air flow rates using an air flow sensor will now be described. In the following description, reference is made to the accompanying drawings, which show by way of illustration specific embodiments in which the invention may be practiced. It is to be understood that changes may be made without departing from the scope of embodiments.

Figure 3:
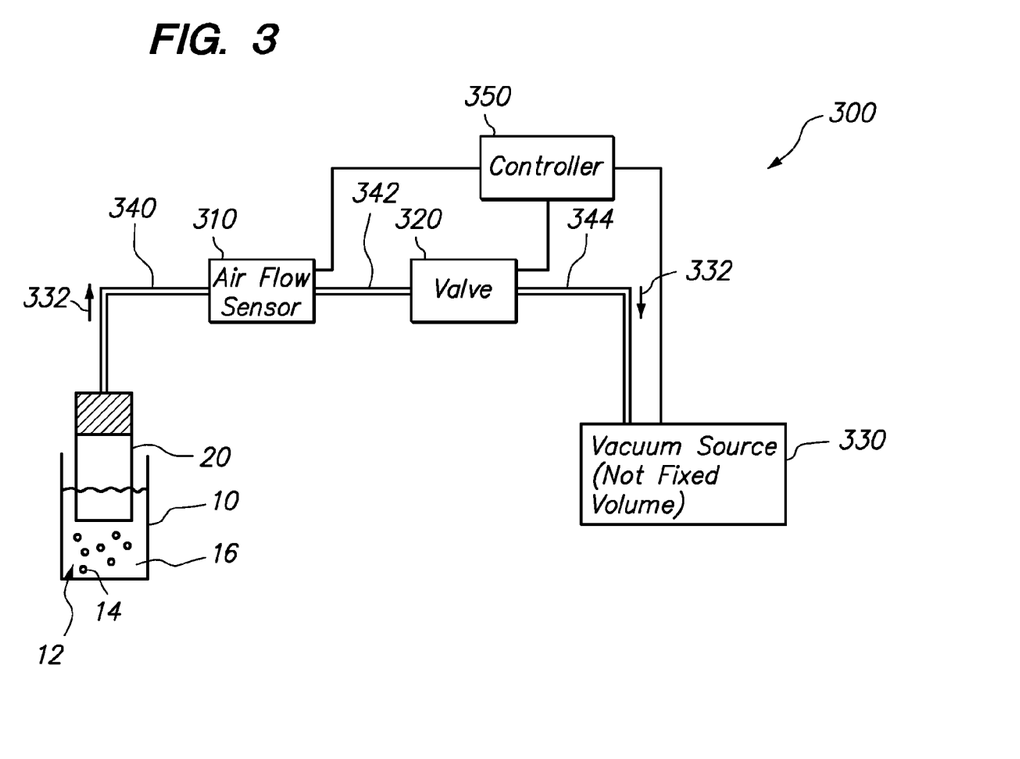
FIG. 3 is illustrates a system for determining how much of a filter is covered by cells of a specimen based on measuring air flow rates through an air flow sensor according to one embodiment of the invention.

Referring to FIG. 3, in accordance with one embodiment, a system 300 for collecting cells 14 from a biological specimen 12 using a filter 20 and determining when sufficient cells 14 have been collected based on air flow rate measurements includes an air flow sensor 310, a valve 320 and a vacuum source 330. The system can, for example, be incorporated into existing slide processing systems, such as in the T5000 available from Cytyc Corporation.

In the illustrated embodiment, the air flow sensor 310 is coupled in-line between a first end or top of the filter 20 and the valve 320 via a connector 340. In an alternative embodiment, the air flow sensor 310 can be coupled in-line between the valve 320 and the vacuum source 330. For purposes of explanation and illustration, not limitation, this specification refers to the air flow sensor 310 being coupled between the filter 20 and the valve 320. The air flow sensor 310 and the valve 320 are coupled together by a connector 342, and the valve 320 and the vacuum source 330 are coupled together by a connector 344. The connectors 340, 342, and 344 can be, for example, vacuum tubes, pressure lines or other suitable connectors that provide a vacuum or negative pressure 332 from the vacuum source 330, through the valve 320 and the air flow sensor 310, and to the filter 20.

It will be appreciated that, although FIG. 1 illustrates separate components, two or more components may be combined into a single component in alternate embodiments. For example, the valve 320 can be integrated within or be a part of the vacuum source 330. For purposes of illustration and explanation, not limitation, this specification refers to and illustrates the individual components.

The air flow sensor 310 measures the rate at which air flows through the air flow sensor 310, e.g., from the filter 20, through the connector 340 and through the air flow sensor 310 (micrograms/second), while cells 14 are collected by the filter 20 during application of vacuum 332. Thus, embodiments of the invention may use a different detection system compared to known systems in order to detect the rate of air flow rather than a vacuum level (as in known systems). Further, these air flow rate measurements are made relative to the vacuum source 330 exterior, rather than with respect to a vacuum level within a vacuum chamber, as is done in known systems.

The air flow rate measurements are provided to a controller 350, such as a micro-controller, processor or computer (generally "controller"). The controller 350 is configured to determine whether the measured air flow rates indicate that enough cells have been collected. The controller 350 can also, as appropriate, open and close the valve 320 and control the vacuum, e.g., change the constant vacuum pressure. Alternatively, these functions can be performed manually.

According to one embodiment, the air flow sensor 310 is a mass air flow sensor. One exemplary mass air flow sensor 310 that can be used with embodiments is AWM90000 series of mass air flow sensors, e.g., Model No. AWM92100V, which has a flow range of +/−200 sccm. These exemplary mass air flow sensors are available from Honeywell, Inc. (Sensing and Controls), 11 West Spring Street, Freeport, Ill. 61032. Other air flow sensors 310 can also be utilized, and embodiments advantageously permit various types of valves 320 to be utilized.

Preferably, although not necessarily, the valve 320 is not a Quick Turn Open (QTO) valve, as is used in known systems, such as the system shown in FIG. 1. While embodiments can be implemented using a QTO valve, embodiments advantageously eliminate the need for a QTO valve and permit other types less costly and less complicated valves 320 to be used since embodiments do not require QTO valves that repeatedly open and close quickly to release vacuum and allow a fixed volume vacuum chamber to re-evacuate. Instead, a regulated open vacuum source 330 may be used that provides a constant level of vacuum or negative pressure 332 (e.g., −0.15 psi), rather than a decaying vacuum level, so that the cells 14 can be collected by opening a valve 320 one time during processing of an individual slide.

Figure 4:
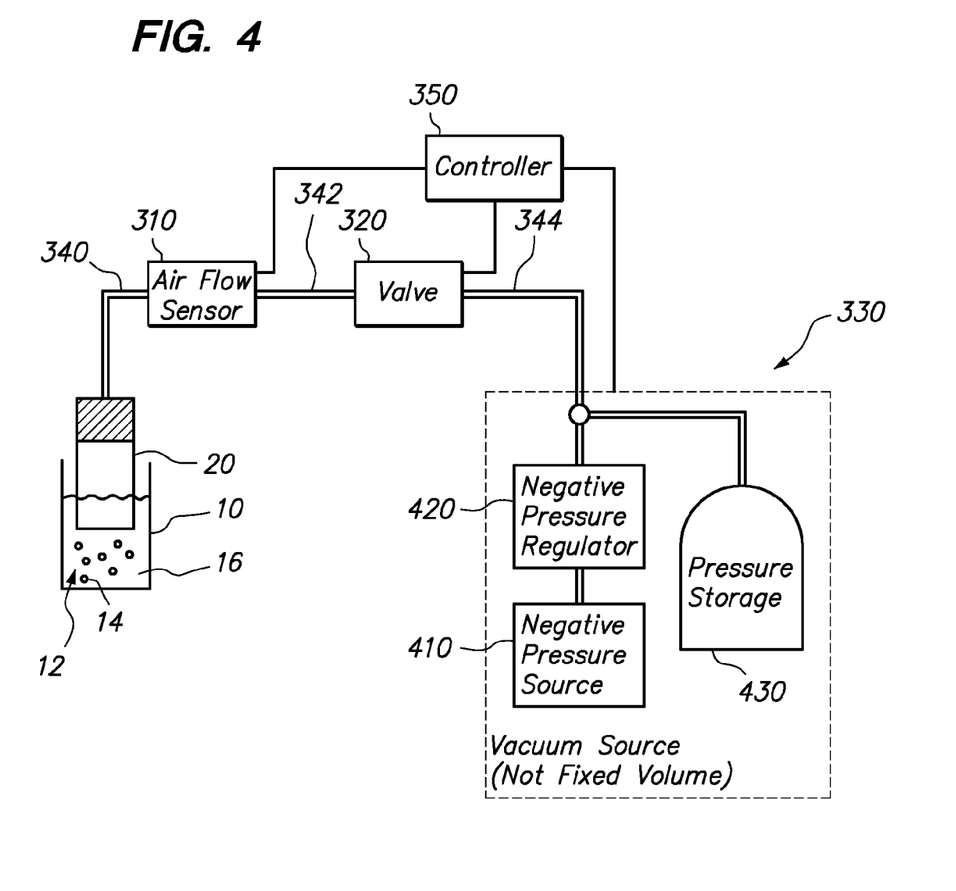
FIG. 4 is a flow chart illustrating a method that is performed using the system shown in FIG. 3.

FIG. 4 illustrates an exemplary open vacuum source 330 that can be used in a system constructed according to one embodiment. The open vacuum source 330 includes a negative pressure source 410 and a regulator 420. The regulator 420 maintains the output of the negative pressure source 410 at a constant vacuum pressure, e.g., −0.15 psi. Thus, the vacuum pressure does not decay over time in contrast to the vacuum pressure resulting from use of a fixed volume chamber. Other vacuum pressures besides −0.15 psi can also be utilized as necessary. Preferably, the vacuum pressure is selected to maintain the cell integrity. The system can also optionally include a pressure storage or secondary source of vacuum 430.

The pressure storage 430 provides initial vacuum pressure to prevent or counteract sudden changes in vacuum pressure in the system. For example, when the valve 320 is initially opened, the pressure storage 430 provides vacuum pressure to ensure that a sudden change in vacuum is not applied to the filter 320. It will be appreciated that various known open vacuum sources 330 can be utilized to implement embodiments of the invention, and that FIG. 4 illustrates one exemplary vacuum source 330.

Figure 5:
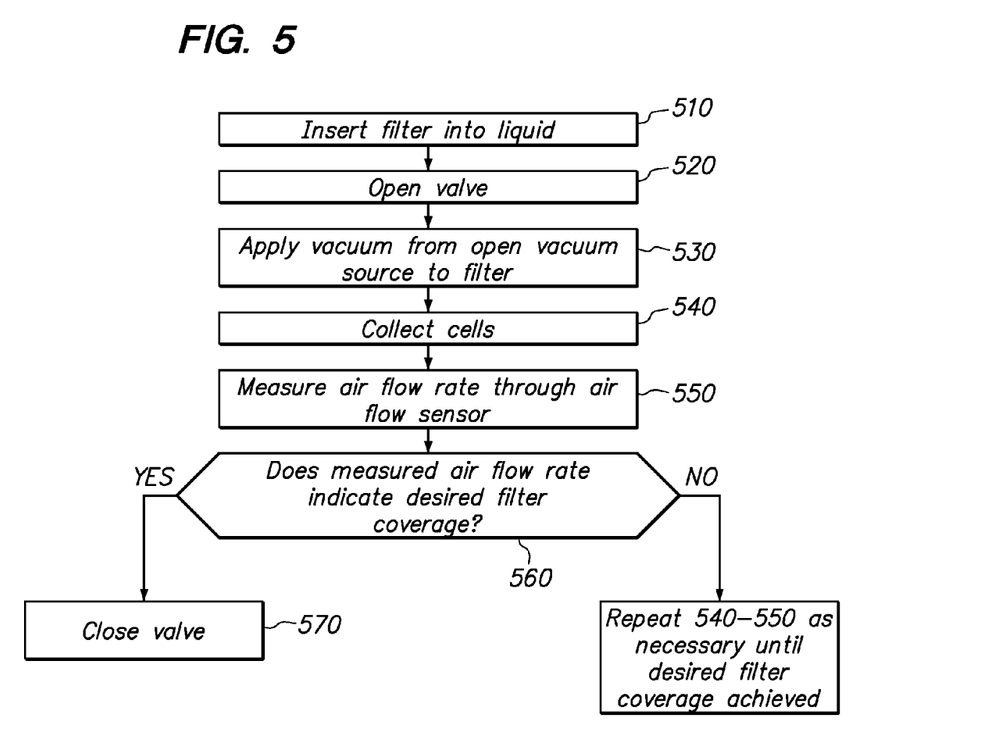
FIG. 5 illustrates the system shown in FIG. 3 and an exemplary vacuum source.

FIG. 5 illustrates a method 500 of collecting cells of a specimen, according to one embodiment, using the system shown in FIG. 4. In step 510, a filter is placed in a liquid containing a specimen. In step 520, a valve is opened, and vacuum is applied to the filter in step 530. In step 540, cells are collected by the filter. In step 550, the air flow rate through the air flow sensor is measured while cells are being collected by the filter. The air flow rate measurements can be performed continuously, periodically (e.g., a 500 Hz or other suitable sampling rate) or intermittently depending on, for example, desired accuracy.

In step 560, having the air flow rate measurement, a determination is made whether the air flow rate has dropped to a certain level or has dropped by a certain amount to indicate that the filter has sufficient cell coverage. If so, then in step 570, the valve can be closed, and the filter can be removed for further processing. If not, then the valve remains open so that additional cells are collected by the filter until the air flow rate measured by the air flow sensor has dropped to certain level or has dropped by a certain amount to indicate that the filter has sufficient cell coverage. Thus, it is not necessary to repeatedly open and close a valve and repeatedly re-evacuate a vacuum chamber. Rather, the valve may be allowed to be opened once to initially collect, and then to remain open to continue collecting cells by application of a fixed vacuum level, until the filter is sufficiently covered with cells.

Figure 6:
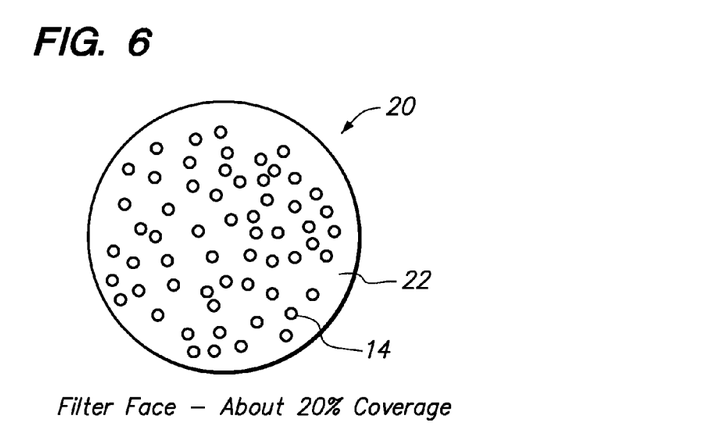
FIG. 6 illustrates a filter face having about 20% cell coverage.
Figure 7:
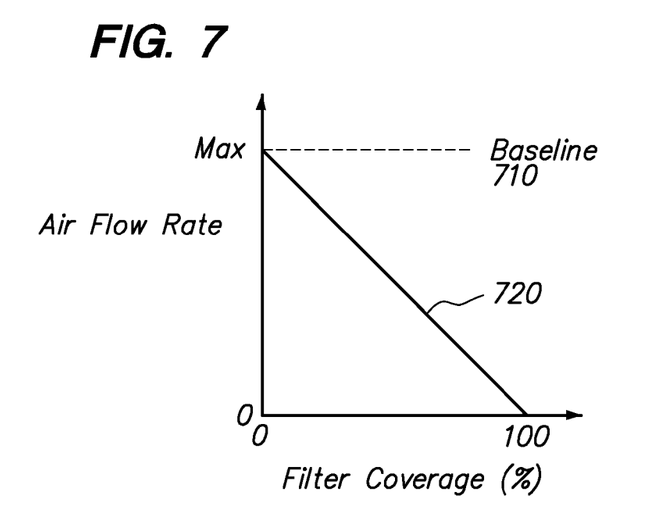
FIG. 7 is graph showing a generally linear relationship between cell coverage on a filter and measured air flow rate.
Figure 8:
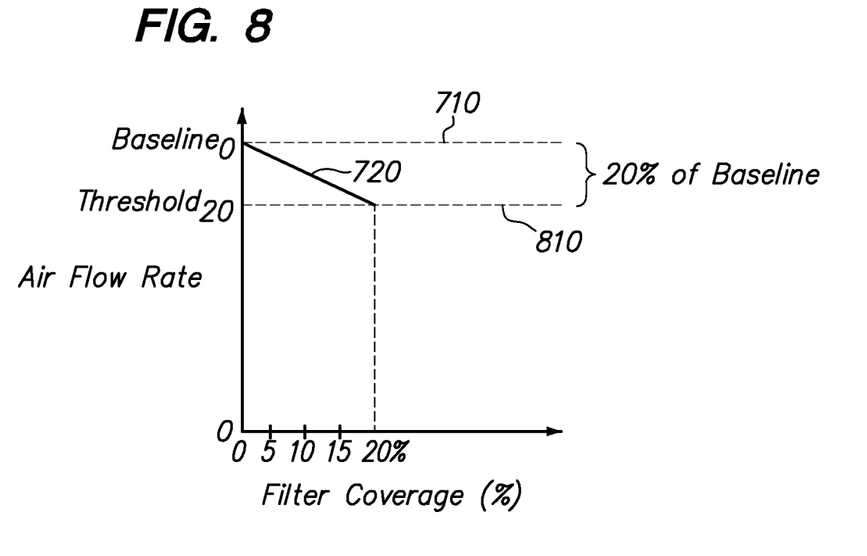
FIG. 8 is a chart further illustrating the relationship between 0-20% cell coverage on a filter and air flow rate.
Figure 9:
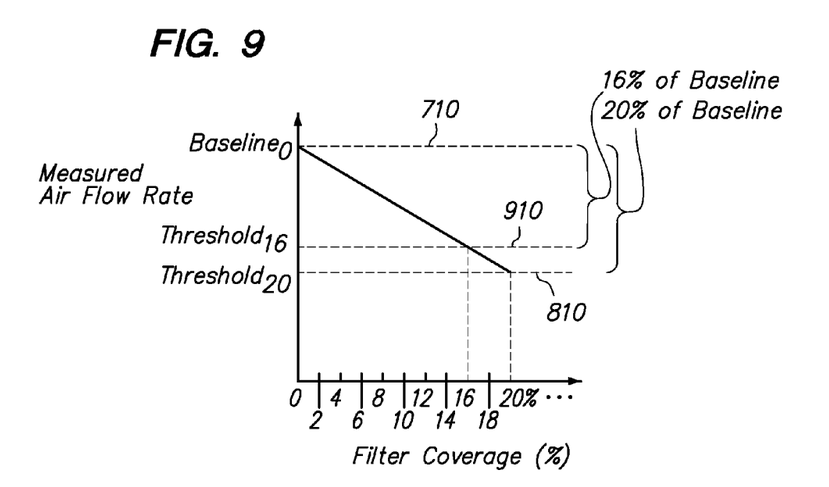
FIG. 9 is a chart further illustrating the relationship between filter coverage and air flow rate and use of different thresholds to indicate different degrees of filter coverage.

The amount of filter coverage that is required may vary depending on the particular application and analysis that is being conducted. FIG. 6 illustrates filter 20 coverage of about 20%, which has been determined to provide a sufficient number of cells 14 without overcrowding. FIGS. 7-9 illustrate in further detail how air flow rates measured by an air flow sensor 310 can be used to determine the amount of filter 20 coverage, whether 20% (as shown in FIG. 6) or other coverage values as needed.

Referring to FIG. 7, the rate of air flow through the air flow sensor 310 is a maximum when no cells 14 are collected by the filter 20 since no portion of the filter 20 is clogged with cells 14. Thus, air can flow freely through the filter 20, and the primary air flow limitation is the filter 20. This air flow rate value can be used as an initial or baseline air flow rate 710. As shown by the line 720 in FIG. 7, as more cells 14 are collected by the filter 20, the air flow through the filter 20 is reduced. Accordingly, the air flow through the air flow sensor 310 is also reduced because less air flows through the filter 20 when collected cells 14 clog filter 20 passageways. Air flow through the filter 20 is blocked when 100% of the filter 20 is covered with cells 14.

As shown in FIG. 7, the line 720 illustrates that the air flow rate generally decreases in a linear manner as the filter 20 collects additional cells 14. Persons skilled in the art will appreciate that there may be some non-linear variations in certain circumstances, but for purposes of illustration, the air flow rate is shown as decreasing linearly as the filter 20 becomes increasingly covered with cells 14.

FIGS. 8 and 9 further illustrate how this linear relationship 720 can be used to determine when a filter 20 has sufficient cell coverage, e.g., when about 16-20% of a filter 20 is covered by cells 14. FIG. 8 illustrates in further detail a portion of the decreasing air flow line 720 shown in FIG. 7 from the point of the filter 20 having no cell coverage (baseline 710) to the point of the filter 20 having about 20% cell coverage (threshold 810). Thus, as cells 14 are collected, the air flow rate eventually drops to the threshold 810 (20% reduction relative to the baseline air flow rate 710), thereby indicating that the filter 20 has about 20% cell coverage. In other words, a threshold 810 air flow rate of 80% of the baseline air flow rate 710 indicates 20% filter coverage. Similarly, as shown in FIG. 9, a 16% reduction 910 in the air flow rate relative to the baseline air flow rate 710 indicates 16% filter coverage.

Persons skilled in the art will appreciate that various thresholds can be used to indicate different filter 20 coverage. Thus, threshold air flow rates of 16%, 18% and 20% of a baseline air flow rate are provided as examples and are not intended to be limiting. It will also be appreciated that the relationship between filter coverage and percentage reduction in air flow relative to the baseline may not be exactly a 1:1 ratio. Thus, the relative numbers and 1:1 ratio are provided for purposes of explanation, not limitation. Persons skilled in the art will also appreciate that the baseline airflow rate 710 can be determined in various ways.

For example, the baseline air flow rate 710 can be provided by the filter manufacturer. Further, a baseline air flow rate 710 can be determined by testing or sipping liquid 16 that does not include any portion of the biological specimen 12. Alternatively, a baseline air flow rate 710 can be determined using a liquid 16 that includes a biological specimen 12, but sipping or sampling a small portion of the liquid 16 that does not include any cells 14.

Figure 10:
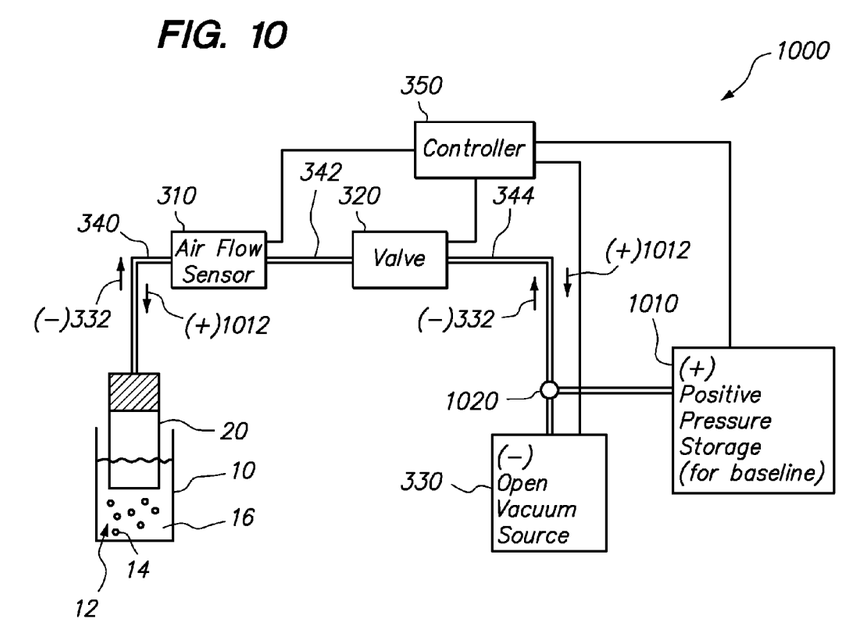
FIG. 10 is illustrates a system for determining filter coverage based on measuring air flow rates through an air flow sensor and for establishing a baseline air flow rate, according to one embodiment.
Figure 11:
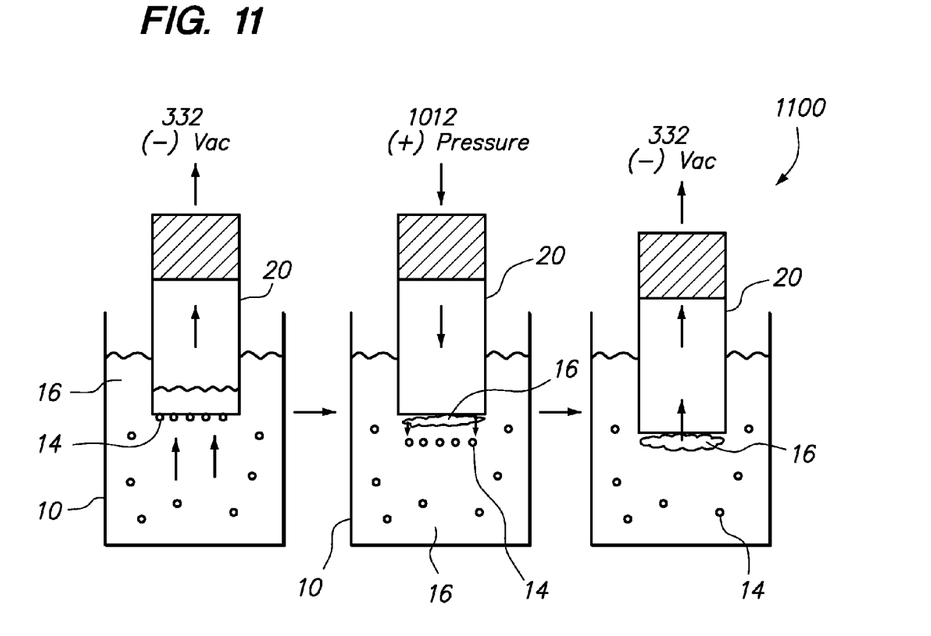
FIG. 11 illustrates one manner of obtaining baseline air flow rate using the system shown in FIG. 10.

For example, FIGS. 10 and 11 illustrate an exemplary system 1000 and method 1100 for obtaining a baseline 710 air flow rate for a filter 20 that is disposed in a liquid 16 having a biological specimen 12. In addition to the regulated open vacuum source 330 (as shown in FIG. 3), a positive pressure source 1010 is provided. In use, as shown in FIGS. 10 and 11, the valve 320 is turned to apply a negative pressure or vacuum 332 from the open vacuum source 330 to the filter 20 to sip fluid 16 from the vial 10. As fluid 16 is drawn up through the filter 20, a small number of cells 14 are collected by the filter 20. Then, a valve 1020 can be turned to disconnect the negative pressure source 330 and connect the positive pressure source 1010, thereby applying a positive pressure 1012 from the positive pressure source 1010 to the filter 20. As a result, cells 14 that were previously collected by the filter 20 are blown or pushed from the filter 20 by the positive pressure 1012. The liquid 16 that was previously drawn up into the filter 20 is also pushed out from the bottom of the filter 20. It is believed that following application of positive pressure 1012, the liquid 16 immediately adjacent to the bottom of the filter 20 contains liquid 16 that is free or substantially free of cells 14.

The positive pressure 1012 is deactivated by turning the valve 1020 to cut off the positive pressure source and apply negative pressure 332 to the filter 20 to sip the liquid 16, i.e., the liquid 16 that is free or substantially free of cells 14. The resulting air flow rate from sipping this cell-free liquid 16 can be used to establish the initial or baseline air flow rate 710. Persons skilled in the art will appreciate that the baseline 710 can be established by sipping a liquid that is free of cells, or sipping a liquid that is substantially free of cells. Then, as additional cells 14 are collected b the filter 20, the degree of filter coverage can be determined by how much the measured air flow rate is below the baseline 710.

Although particular embodiments have been shown and described, it should be understood that the above discussion is intended to illustrate, but not limit the scope of these embodiments, and various changes and modifications may be made to the respective embodiments without departing from the scope of the claims set forth below.

For example, the air flow sensor can be coupled between different components, e.g., between the filter and the valve, and between the valve and the vacuum sources. Various open vacuum sources can also be utilized, and various systems and methods can be used to establish a baseline air flow. Further, determinations regarding filter coverage using an air flow sensor can be made relative to a baseline or based on the air flow dropping to a certain level independent of a baseline. For example, determinations regarding filter coverage can be made based on a percentage change or drop in air flow relative to a baseline air flow. Alternatively, determinations regarding filter coverage can be made based on the measured air flow dropping below a particular rate or value). Thus, determinations can be made relative to and/or independently of a baseline air flow.

What is claimed is:

1. A method of collecting cells on a filter disposed in a specimen fluid containing suspended cells of a biological specimen, the method comprising:
   applying a vacuum across the filter disposed in the specimen fluid using a vacuum source, thereby collecting specimen cells from the fluid on a surface of the filter;
   measuring a rate of air flow between the filter and the vacuum source while the vacuum is being applied; and
   determining when a sufficient amount of cells have been collected on the filter based on the measured air flow rate.

2. The method of claim 1, wherein the applied vacuum is substantially constant.

3. The method of claim 1, wherein the air flow rate is measured using a mass air flow sensor.

4. The method of claim 3, wherein the mass air flow sensor is positioned between the filter and a valve that controls application of the vacuum.

5. The method of claim 3, wherein the mass air flow sensor is positioned between the vacuum source and a valve that controls application of the vacuum, the valve being located between the mass air flow sensor and the filter.

6. The method of claim 1, wherein determining whether sufficient cells have been collected on the filter comprises determining when the measured air flow rate drops below a threshold air flow rate.

7. The method of claim 6, wherein the threshold air flow rate is determined relative to a baseline air flow rate.

8. The method of claim 7, wherein the threshold air flow rate is about 80% of the baseline air flow rate.

9. The method of claim 7, wherein about 20% of the filter surface is covered with specimen cells when the measured air flow rate is about 80% of the baseline air flow rate.

10. The method of claim 7, wherein the baseline air flow rate is determined by measuring an air flow rate across the filter while the filter is suspended in a portion of the specimen fluid that is substantially free of cells.

11. A method of collecting cells on a filter disposed in a specimen fluid containing suspended cells of a biological specimen, the method comprising:
    determining a baseline air flow rate between the filter and the vacuum source while the filter is suspended in a portion of the specimen fluid that contains relatively few, if any, suspended cells;
    applying a vacuum across the filter disposed in the specimen fluid using a vacuum source, thereby collecting specimen cells from the specimen fluid on a distal facing surface of the filter;
    monitoring a rate of air flow between the filter and the vacuum source while the vacuum is being applied; and
    determining when a sufficient amount of cells have been collected on the filter based on the monitored air flow rate dropping below the baseline air flow rate by a predetermined amount.

12. The method of claim 11, wherein the predetermined amount is about 80% of the determined baseline air flow rate.

13. The method of claim 12, wherein about 20% of the filter surface is covered with cells when the monitored air flow rate is about 80% of the baseline air flow rate.

14. The method of claim 11, wherein the applied vacuum is substantially constant.

15. The method of claim 11, wherein the air flow rate is monitored using a mass air flow sensor positioned between the filter and a valve that controls application of the vacuum.

16. The method of claim 11, wherein the air flow rate is monitored using mass air flow sensor positioned between the vacuum source and a valve that controls application of the vacuum, the valve being located between the mass air flow sensor and the filter.

* * * * *